(12) United States Patent
Yu et al.

(10) Patent No.: US 8,833,146 B2
(45) Date of Patent: Sep. 16, 2014

(54) CORROSION SENSOR

(75) Inventors: Hui Yu, San Antonio, TX (US); Leonardo Caseres, Helotes, TX (US)

(73) Assignee: Southwest Research Institute, San Antonio, TX (US)

( * ) Notice: Subject to any disclaimer, the term of this patent is extended or adjusted under 35 U.S.C. 154(b) by 399 days.

(21) Appl. No.: 12/767,313

(22) Filed: Apr. 26, 2010

(65) Prior Publication Data

US 2011/0259092 A1    Oct. 27, 2011

(51) Int. Cl.
*G01N 17/00*    (2006.01)
*G01N 17/02*    (2006.01)

(52) U.S. Cl.
CPC ........................ *G01N 17/02* (2013.01)
USPC ................................................... 73/86

(58) Field of Classification Search
CPC .................. G01N 17/04; G01N 17/00
See application file for complete search history.

(56) References Cited

U.S. PATENT DOCUMENTS

| | | | | |
|---|---|---|---|---|
| 3,660,249 A | * | 5/1972 | Townsend | 205/775.5 |
| 4,264,424 A | * | 4/1981 | Niedrach | 204/421 |
| 5,071,537 A | * | 12/1991 | Yamaguchi et al. | 204/414 |
| 5,306,414 A | * | 4/1994 | Glass et al. | 204/404 |
| 5,320,735 A | * | 6/1994 | Kato et al. | 204/419 |
| 5,382,331 A | * | 1/1995 | Banks | 205/781 |
| 6,572,748 B1 | | 6/2003 | Herrmann et al. | |
| 6,673,222 B1 | * | 1/2004 | Papavinasam et al. | 204/404 |
| 6,987,396 B2 | | 1/2006 | Yang et al. | |
| 2005/0005676 A1 | * | 1/2005 | Crawley et al. | 73/24.01 |
| 2008/0149482 A1 | * | 6/2008 | Marett et al. | 204/414 |

OTHER PUBLICATIONS

Alonso et al., Chloride threshold dependence of pitting potential of reinforcements, Electrochimica Acta, 2002, pp. 3469-3481, 47.
Alonso et al., Chloride threshold values to depassivate reinforcing bars embedded in a standardized OPC mortar, Cement and Concrete Research, 2000, pp. 1047-1055, 30.
Anderko et al., An Electrochemical Approach to Predicting and Monitoring Localized Corrosion in Chemical Process Streams, Corrosion 2003, pp. 1-24, Paper No. 03375.
Andringa et al., Unpowered Wireless Corrosion Sensor for Steel Reinforced Concrete, IEEE Xplore, 2005, pp. 155-158.
Arya et al., Factors Influencing Chloride-Binding in Concrete, Cement and Concrete Research, 1990, pp. 291-300, vol. 20.
Caseres, In-Situ Leaching for Determination of Chloride and pH in Concrete and Mortar Pore Water, A Thesis submitted in partial fulfillment of the requirements for the degree of Master of Science in Civil Engineering, Department of Civil and Environmental Engineering, College of Engineering, University of South Florida, Nov. 5, 2002, 189 pages.

(Continued)

*Primary Examiner* — Peter MacChiarolo
*Assistant Examiner* — Alex Devito
(74) *Attorney, Agent, or Firm* — Grossman, Tucker et al

(57) ABSTRACT

A corrosion sensor may include a sensor body, a chloride probe held in the sensor body, a pH probe held in the sensor body, a reference electrode for the chloride probe and the pH probe held in the sensor body, a multiple array sensor held in the sensor body and a resistivity probe held in the sensor body. A method of measuring corrosion in a reinforced concrete structure may include inserting a corrosion sensor into a reinforced concrete structure and monitoring chloride ions with the chloride probe, pH with the pH probe, localized concrete resistivity with the resistivity probe and corrosion current density with the multiple array sensor.

18 Claims, 20 Drawing Sheets

(56) References Cited

OTHER PUBLICATIONS

Carkhuff et al., Corrosion sensors for concrete bridges, IEEE Xplore, Jun. 2003, 1 pg abstract, vol. 6 Issue 2.

Duffó et al., Characterization of Solid embeddable reference electrodes for corrosion monitoring in reinforced concrete structures, Electrochimica Acta, 2009, pp. 1010-1020, 54.

Glass et al., The Presentation of the Chloride Threshold Level for Corrosion of Steel in Concrete, Corrosion Science, 1997, pp. 1001-1012, vol. 39, No. 5.

Hu et al., A Comprehensive Study of the Corrosion Behavior for Reinforced Steel in Concrete, 16th International Corrosion Congress, Sep. 19-24, 2005, 6 pages.

Kelly et al., Development of an Embeddable Microinstrument for Corrosivity Monitoring in Concrete, Virginia Transportation Research Council, Jul. 1999, 42 pages.

Kollár et al., Complicated Procedures Made Easy—Implementing a graphical user interface and automatic procedures for easier identification and modeling, IEEE Instrumentation & Measurement Magazine, Sep. 2003, 8 pages.

Luping et al., Chloride Binding Capacity and Binding Isotherms of OPC Pastes and Mortars, Cement and Concrete Research, 1993, pp. 247-253, vol. 23.

Montemor et al., Monitoring of the chloride content in reinforced concrete structures using a Ag/AgCl-based sensor. Laboratory and field tests, 16th International Corrosion Congress, Sep. 19-24, 2005, 6 pages.

Myrdal, The electrochemistry and characteristics of embeddable reference electrodes for concrete, European Federation of Corrosion Publications, 2007, 33 pages, No. 43.

Rasheeduzzafar et al., Effect of Tricalcium Aluminate Content of Cement on Chloride Binding and Corrosion of Reinforcing Steel in Concrete, ACI Materials Journal, Jan.-Feb. 1992, pp. 3-12, Title No. 89-M1.

Reis et al., Evaluation of the VTI ECI-1 Embedded Corrosion Instrument, State of California, Department of Transportation, Materials Engineering and Testing Services, Office of Testing and Technology Services Corrosion Technology Branch, Jan. 2006, 64 pages.

Shams et al., Wireless Power Transmission to a Buried Sensor in Concrete, IEEE Sensors Journal, Dec. 2007, pp. 1573-1577, vol. 7, No. 12.

Srinivasan et al., A Wireless Sensor for Monitoring Corrosion and Chloride Ingress in Concrete, The Johns Hopkins University Applied Physics Laboratory, date unknown, 1 page.

Srinivasan et al., Miniature Wireless Full Spectrum EIS Corrosion Sensor, 2005 Tri-Service Corrosion Conference, 2005, pp. 1-11.

Tan, Wire beam electrode: A new tool for studying localised corrosion and other heterogeneous electrochemical processes, Corrosion Science, 1999, pp. 229-247, 41.

Watters., et al., Smart Pebbles™: Passive Embeddable Wireless Sensors for Chloride Ingress Monitoring in Bridge Decks, State of California Department of Transportation, Technical Report Documentation Page, Jun. 30, 2003, pp. 1-60.

Watters., et al., Smart Pebble: wireless sensors for structural health monitoring of bridge decks, SPIE Digital Library, Sep. 9, 2003, 1 page abstract, vol. 5057.

Yang et al., An In-Situ Galvanically Coupled Multielectrode Array Sensor for Localized Corrosion, Corrosion Science Section, Dec. 2002, pp. 1004-1014.

Yang et al., Comparison of Localized Corrosion of Fe—Ni—Cr—Mo Alloys in Chloride Solutions Using a Coupled Multielectrode Array Sensor, Corrosion 2002, pp. 1-14, Paper No. 02545.

Yang et al., Coupled Multielectrode Online Corrosion Sensor, Chemical Treatment—Materials Performance, Sep. 2003, pp. 48-52.

Yang et al., Development of a Multi-Electrode Array Sensor for Monitoring Localized Corrosion, Proceedings of the Extended Abstract, The Electrochemical Society, 2001, 1 page.

Yang et al., Evaluation of Corrosion Inhibitors in Cooling Water Systems Using a Coupled Multielectrode Array Sensor, Corrosion 2002, pp. 1-17, Paper No. 02004.

\* cited by examiner

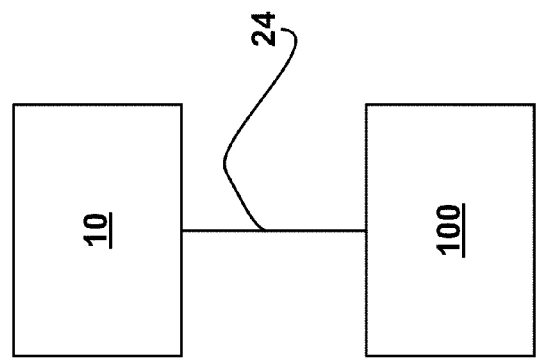

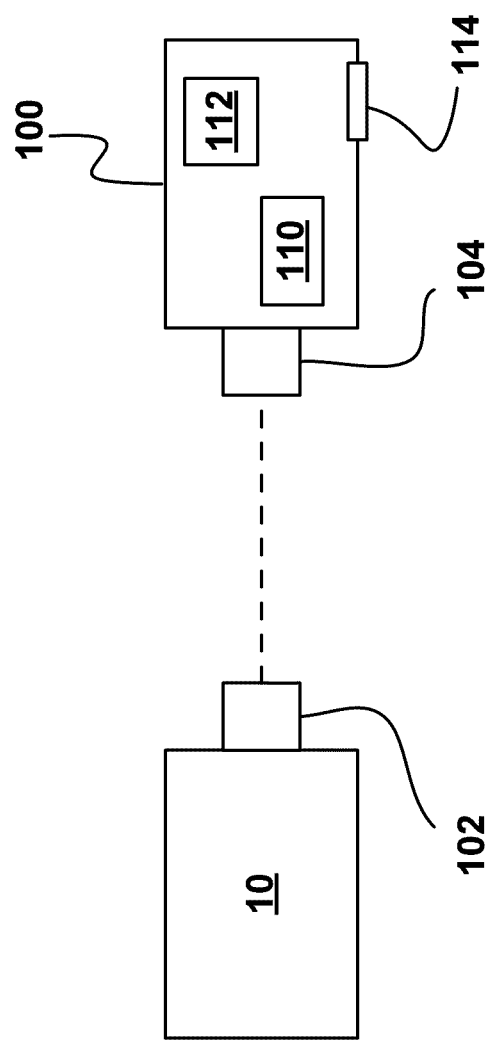

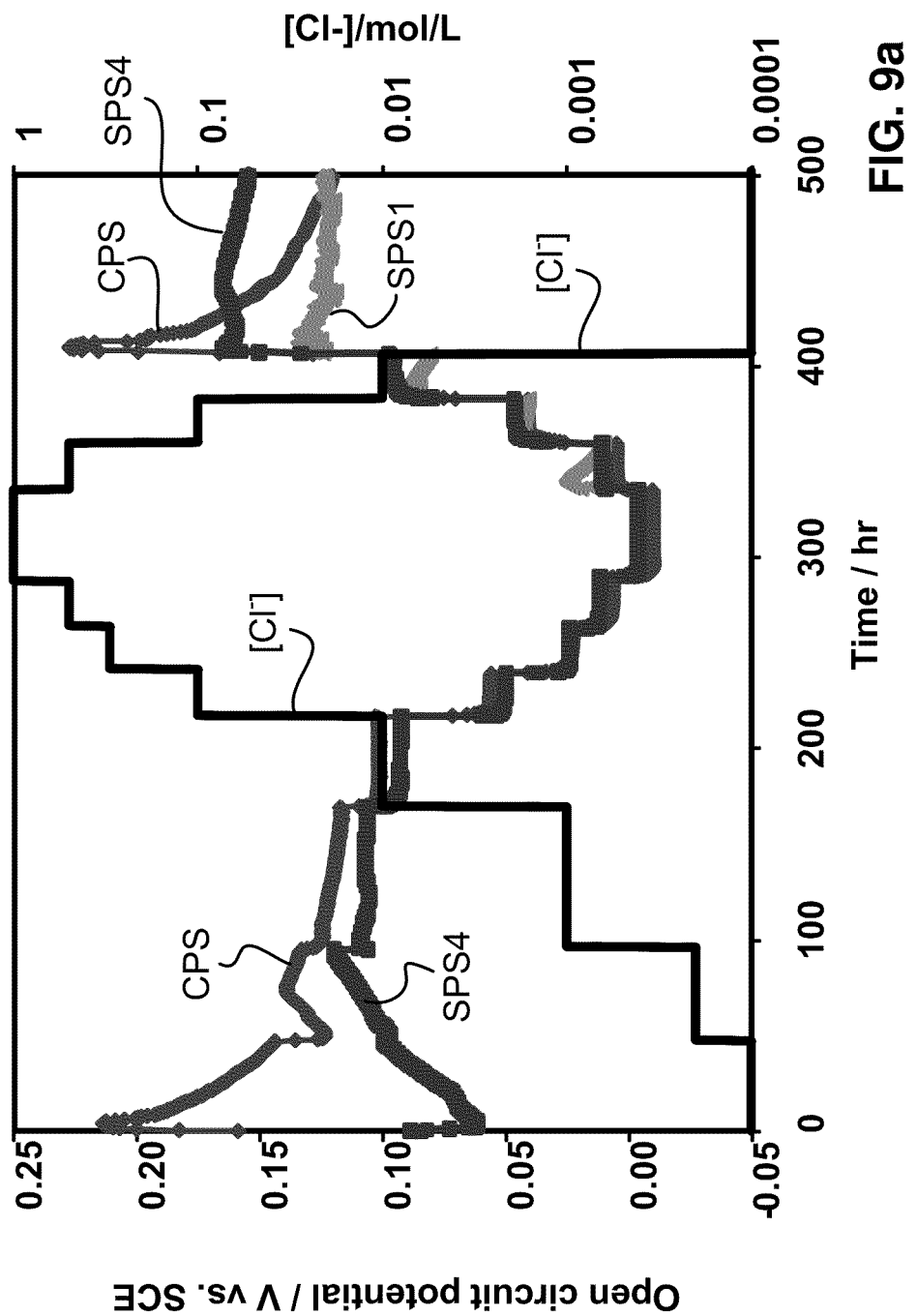

CORROSION SENSOR

FIELD OF THE INVENTION

The present disclosure relates to a corrosion sensor that may be embedded in reinforced concrete structures and, in particular, a corrosion sensor that may measure chloride concentration, pH, localized concrete resistivity and/or corrosion rates to monitor the corrosion state of a reinforced concrete structure.

BACKGROUND

Reinforced concrete structures, particularly in northern and coastal states, may commonly be exposed to chlorides either from de-icing salts and/or seawater. Chloride-induced corrosion has been considered a major cause of premature failure of such structures. Chloride-induced corrosion affects the reinforcing structure of the concrete, such as rebar, grids or plates that may be used in the concrete structure. The chloride ions may cause the passivating layer that forms on the reinforcing structure to become permeable allowing for further oxidation and corrosion of the reinforcing structure. In addition, the character of the concrete material may be affected, wherein an acidic environment may develop and remove the passivating layer that forms on the reinforcing structure. The corrosion products may exhibit a volume greater than the initial volume of the original reinforcing structure, which may eventually cause cracking and spallation of the concrete due to expansion caused by the corrosion products.

As reinforced concrete is used in many infrastructure projects, such as bridges and highways, monitoring the corrosion of these structures may be of relative significance. For example, the National Highway Bridges Reconstruction and Inspection Act passed Jul. 25, 2008 mandates annual inspections of structurally deficient highway bridges. Parameters of interest include not only concentration of chloride but also, other deleterious ion species and the character of the concrete material itself.

SUMMARY

An aspect of the present disclosure relates to a corrosion sensor. The corrosion sensor may include a sensor body, a chloride probe held in the sensor body, a pH probe held in the sensor body, a reference electrode for the chloride probe and the pH probe held in the sensor body, a multiple array corrosion rate sensor held in the sensor body and a resistivity probe held in the sensor body.

Another aspect of the present disclosure relates to a method of measuring corrosion-status of a reinforced concrete structure. The method may include inserting a corrosion sensor into a reinforced concrete structure and monitoring chloride ions with the chloride probe, pH with the pH probe, localized concrete resistivity with the resistivity probe and rebar corrosion current density with the multiple array sensor. The corrosion sensor may include a sensor body, a chloride probe held in the sensor body, a pH probe held in the sensor body, a reference electrode for the chloride probe and the pH probe held in the sensor body, a multiple array sensor held in the sensor body and a resistivity probe held in the sensor body.

A further aspect of the present disclosure relates to a system for monitoring corrosion-status of a reinforced concrete structure. The system may include at least one corrosion sensor and a data acquisition system in communication with the at least one corrosion sensor. The corrosion sensor may include a sensor body, a chloride probe held in the sensor body, a pH probe held in the sensor body, a reference electrode for the chloride probe and the pH probe held in the sensor body, a multiple array corrosion rate sensor held in the sensor body and a resistivity probe held in the sensor body.

BRIEF DESCRIPTION OF THE DRAWINGS

The above-mentioned and other features of this disclosure, and the manner of attaining them, will become more apparent and better understood by reference to the following description of embodiments described herein taken in conjunction with the accompanying drawings, wherein:

FIG. 7 illustrates an embodiment of a corrosion sensor in electrical communication with a data acquisition system;
FIG. 8 illustrates an embodiment of a corrosion sensor in wireless communication with a data acquisition system;
FIG. 9a illustrates the open current potential versus voltage over a period of approximately 500 hours, wherein chloride ions are introduced over the time period for a number of the simulated concrete pour solutions.

DETAILED DESCRIPTION

Figure 1:
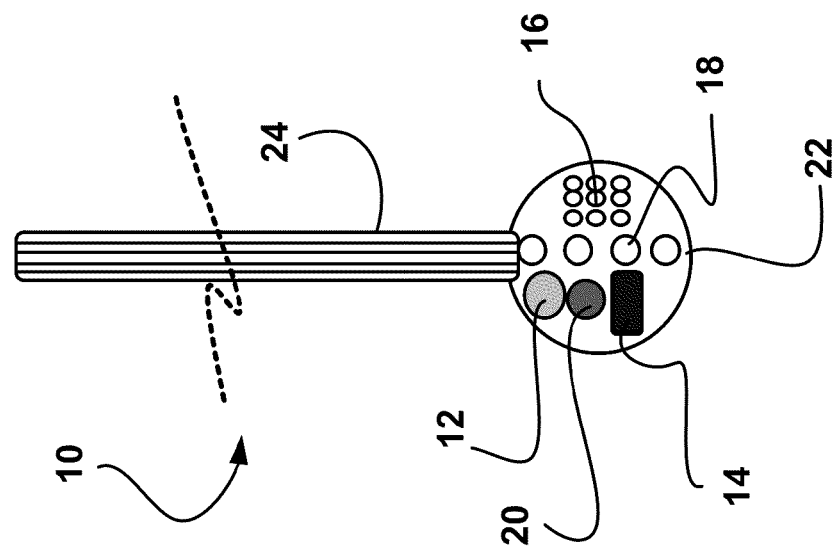
FIG. 1 illustrates an embodiment of a corrosion sensor.

It is to be understood that this disclosure is not limited in its application to the details of construction and the arrangement of components set forth in the following description or illustrated in the drawings. The embodiments herein are capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "coupled," and "mounted," and variations thereof herein are used broadly and encompass direct and indirect connections, couplings, and mountings. In addition, the terms "connected" and "coupled" and variations thereof are not restricted to physical or mechanical connections or couplings.

The present disclosure relates to a corrosion sensor that may be embedded in reinforced concrete structures and, in particular, a corrosion sensor that may measure chloride concentration, pH, localized concrete resistivity and corrosion rates to monitor a corrosion state of the reinforcing structure in the concrete. As noted above, reinforced concrete structures may include various reinforcing materials such as rebar, grids, plates, or fibers. Such reinforcing materials may be formed from steel, iron, or other materials. When the reinforcing material is formed from steel or iron, a passivating layer of iron oxide may form on the reinforcing material, which prevents further oxidation and/or corrosion. However, failure of the reinforced concrete structure may occur should the passivating layer be breached and further corrosion occurs. In addition, localized concrete resistivity may be understood as resistivity in an area proximal to the sensor. For example, it may be in the concrete adjacent to the sensor.

A number of parameters have been identified as indicators of the reduction of the passivating layer formed on the reinforcing structure. For example, the presence of chloride ions has been identified as a parameter indicating the reduction in the passivating layer as the chloride ions cause the passivating layer to become permeable. A reduction of pH may also act as an indicator of potential changes in the passivity of the reinforcing material. In addition, the concrete resistivity has been identified as a parameter to characterize the resistance of the concrete to deleterious ions. Further, indicators of the corrosion rate or corrosion current density may be utilized to determine the integrity of the reinforced concrete.

Thus, the corrosion sensor may include a number of probes including at least one chloride sensing probe, at least one pH probe, at least one corrosion rate probe and/or at least one resistivity probe. One or more corrosion sensors may be embedded in reinforced concrete structures at varying depths underneath the surface of the concrete. The corrosion sensor may be used in combination with a data acquisition system and/or other devices to monitor corrosion periodically or continuously over an extended time period. Communication between the corrosion sensor and the data acquisition devices may be wireless or wired.

FIG. 1 illustrates an embodiment of a corrosion sensor 10. The corrosion sensor may include, for example, a chloride probe 12, a pH probe 14, a multiple array corrosion rate sensor 16 and/or a localized concrete resistivity probe 18. In addition, a reference electrode 20 may be provided for chloride and pH measurements. The probes may be embedded or at least partially encapsulated in a carrier 22. In addition, each probe may include one or more electrical connections 24 for communication purposes.

The chloride probe 12 may be formed from a redox electrode where the potential developed may be used to identify a chloride concentration. A redox electrode may be understood as an electrode that may be used in electrochemical measurements, wherein a reaction occurs between a metal and its salt upon exposure to a given environment. An embodiment of a redox electrode may include a silver/silver chloride electrode. The reaction between the silver and it's salt may be understood as follows:

$$Ag^+ + 1e^- \leftrightarrow Ag^0(s) \quad \text{Eq.1}$$

$$Ag^+ + Cl^- \leftrightarrow AgCl(s) \quad \text{Eq.2}$$

Wherein the overall reaction may be understood as follows:

$$Ag^0(s) + Cl^- \leftrightarrow AgCl(s) + e^- \quad \text{Eq.3}$$

A silver/silver chloride electrode may be produced by, in one embodiment, dipping a commercially pure silver rod into a bath of molten silver chloride, wherein the bath may be, for example, at a temperature of in the range of 450° C. to 500° C., such as 455° C., 460° C., etc. The silver rod may be dipped a number of times, such as two to ten times, including all values and increments therein. For example, the silver rod may be dipped four times. The number of times the dipping process is repeated may be dependent upon the compactness and/or smoothness of the coating. Once the AgCl layer is formed, the electrode may cleaned with acetone and dried.

Figure 2:
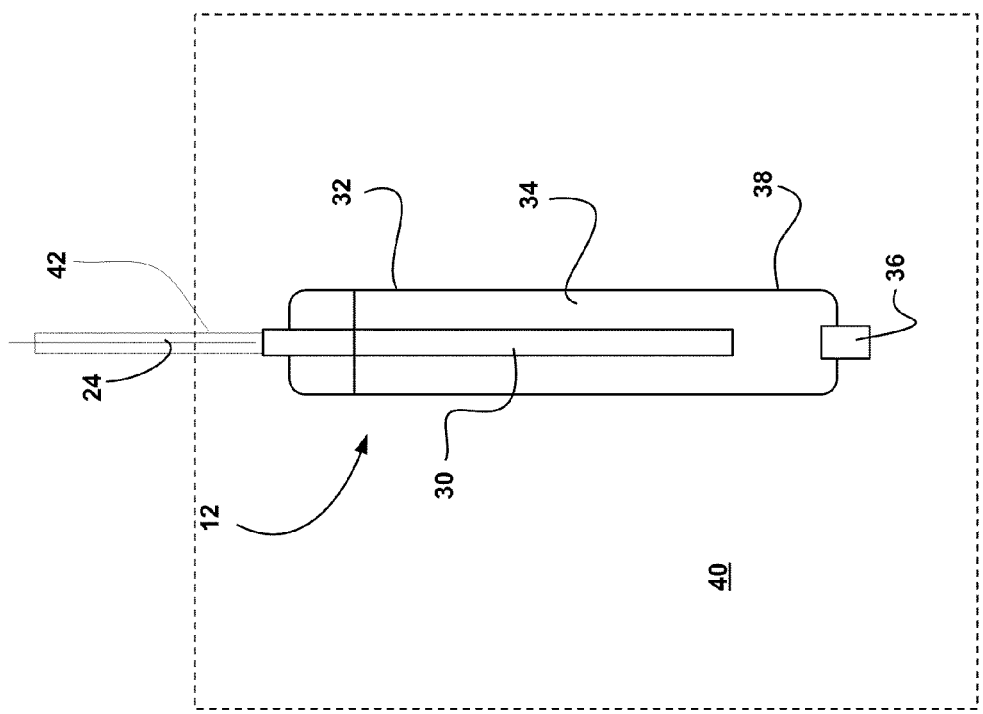
FIG. 2 illustrates an embodiment of a chloride probe.

An embodiment of a chloride probe 12, as illustrated in FIG. 2, includes an electrode 30, which may be encapsulated in a cell 32. The cell 32 may be formed from glass, polyethylene, or another polymeric material that may be inert to the environments in which the corrosion sensor may be exposed. The cell 32 may be filled or saturated with an internal filling solution 34, which may include a liquid or gel composition. The internal filling solution 34 may include, for example, saturated potassium nitrate ($KNO_3$) gel. The saturated $KNO_3$ gel may include for example, water and thickeners such as hydroxyethyl cellulose, as well as compositions such as ethylene glycol. Other internal filling solution 34 may include potassium sulfate ($K_2SO_4$). In addition, a porous junction 36 may be formed in the wall 38 of the cell 32 to provide a junction between the internal filling solution 34 and the external test solution, or reinforced concrete environment 40. The porous junction 36 may be formed of zirconium powder, glass frit, quartz, porous ceramics, etc. Use of zirconium powder may minimize the penetration of $OH^-$ ions into the cell. It may be appreciated that in some embodiments, the porous junction 36 may not always be necessary and its presence may depend on the electrolyte 34.

An electrical connection may be provided to the electrode 30 of the chloride probe 12. The electrical connection 24 may be covered with a sheath 42. The electrical connection 24 may include, for example, a wire, which may be formed of copper, gold or another conductive material such as aluminum, nickel, etc. The sheath 42 may cover at least a portion of the electrical connection 24 and may be formed of a polymer material such as epoxy, urethane, fluoropolymers such as polytetrafluoroethylene or ethylene-tetrafluoroethylene, silicone rubber, polyethylene, crosslinked polyethylene, polypropylene, etc. The exposed area of the electrode 30 may be in the range of 0.1 $cm^2$ to 2 $cm^2$, including all values and increments therein, such as 1 $cm^2$. A reference electrode 20 may also be provided in contact with the external test solution or reinforced concrete environment 40. The reference electrode may be formed of graphite, gold or platinum.

Figure 3:
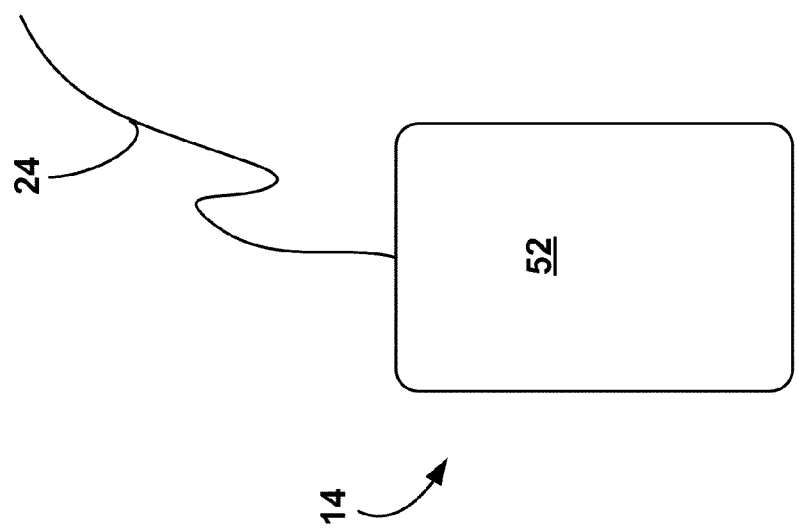
FIG. 3 illustrates an embodiment of a pH probe.

As note above, a pH probe 14 may also be provided in the corrosion sensor. As illustrated in FIG. 3, the pH probe 14 may include a pH sensing body 52. The pH sensing body 52 may be formed of, for example, $Ir_2O_3/Ta_2O_5$. The redox equilibriums of $Ir_2O_3/Ta_2O_5$ may be understood as follows:

$$Ir_2O_3 + 3H_2O + 6e^- \leftrightarrow 2Ir + 6OH^-; \quad \text{Eq.4}$$

and $$Ta_2O_5 + 10H^+ + 10e^- \leftrightarrow 2Ta + 5H_2O. \quad \text{Eq.5}$$

Other probe compositions may include, for example, Ag/AgCl or mixed-metallic oxide coatings such as Iridium/Iridium Oxide (Ir/Ir$_2$O$_3$). The pH probe 14 may also be connected via an electrical connection 24. The electrical connection may be the same as or a different connection from the connection to the chloride probe 12. Furthermore, the electrical connection to the pH probe and the electrical connection to the chloride probe 12 may be in the form of a ribbon cable. Again, the electrical connection may be via a wire made out of materials such as copper, gold, silver or other conductive materials such as aluminum, nickel, etc. A reference electrode 20 (FIG. 1) may also be provided. The reference electrode may be a shared reference electrode 20 with the chloride probe 12 (as illustrated) or may be a separate reference electrode. The reference electrode may again be formed of graphite, gold or platinum.

Figure 4:
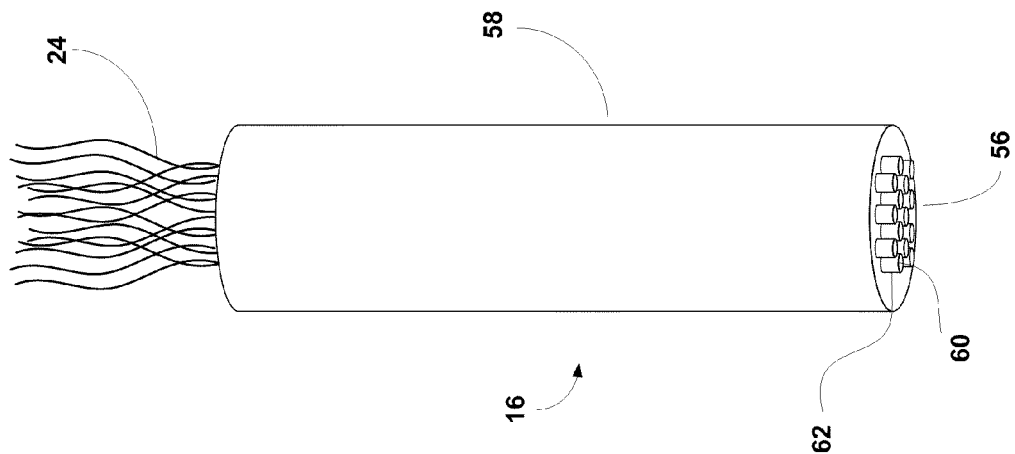
FIG. 4 illustrates an embodiment of a multiple array sensor probe.

A multiple array sensor probe 16 may be provided to measure corrosion current density, i.e., corrosion rate. An embodiment of the multiple array sensor 16 is illustrated in FIG. 4. The multiple array sensor may include two or more sensing elements 56. For example, the multiple sensor array may include up to 100 sensing elements 56, including all values and increments in the range of two to 100 sensing elements 56 or in the range of 2 to 20 elements, or 16 elements or 9 elements. The sensing elements 56 may be formed from a material having a similar corrosion rate in a selected environment as the corrosion rate of the material of interest (i.e., the reinforcing structure of the concrete). For example, in one embodiment, the multiple array sensor 16 may be formed from 1018 carbon steel. In one embodiment, the sensing elements 56 may have a diameter in the range of 0.01 cm to 1.0 cm, including all values and increments therein. The sensing elements 56 may have a length of 0.01 cm or greater, depending on the size of the corrosion sensor. For example, in one embodiment, the sensing elements 56 may have a length of 0.01 cm to 10 cm, including all values and increments therein.

The sensing elements 56 of the multiple array sensor may be embedded in a polymeric material matrix 58, such as, for example, epoxy (for example, product number 2300 from Aremco Products, Inc.), polyethylene, crosslinked polyethylene, ultrahigh molecular weight polyethylene, fluoropolymers such as polytetrafluoroethylene, ethylene tetrafluoroethylene, etc. The polymer material matrix 58 may exhibit a temperature resistance in the range of −55° C. to 175° C., including all values and increments therein. Furthermore, the polymer material matrix 58 may exhibit a compressive yield strength in the range of 15 MPa or greater, such as in the range of 14 MPa to 300 MPa, including all values and increments therein. The sensing elements 56 may be embedded in the polymer matrix 58 such that a known surface area of the element may be exposed. For example, in one embodiment, the exposed surface area may include or be limited to an end or tip 60 of the sensing element 56, and may equal the cross-sectional area of the sensing element, such that the surface of the tip may be coplanar or coextensive with the surface of the multiple array sensor 16. In another embodiment, the exposed surface area may include the tip 60 of the sensing element as well as a portion of the sensing element shaft or longitudinal surfaces 62. The sensing elements 56 may be grouped together wherein the sensors may be spaced in the range of 0.01 cm to 1 cm from center point to center point, including all values and increments therein. In some embodiments, the sensing elements 56 may be separated by other probes 12 and 14. Again, electrical connections 24 may be affixed to each sensing element 56. The electrical connections 24 may be the same as or different from those used in the other probes. Further, the electrical connections 24 may be joined into a ribbon connector.

Figure 5:
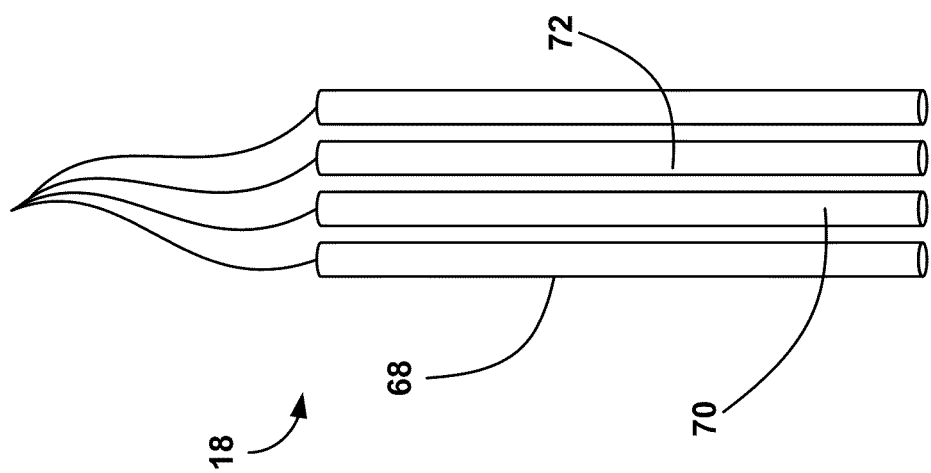
FIG. 5 illustrates an embodiment of a resistivity probe.

A resistivity probe 18 may also be included in the corrosion sensor 10 which may measure the resistivity of the concrete surroundings. The resistivity probe 18 may include at least two conductivity sensors, including all values and increments in the range of 2 to 10. For example, in some embodiments, the resistivity probe 18 may include 3 conductivity sensors and, in some embodiments, the resistivity probe 18 may include 4 conductivity sensors 68, as illustrated in FIG. 5. The conductivity sensors 68 may include at least one drive electrode 70, upon which a voltage may be applied, and at least one conductivity sensing electrode 72, by which a resulting current is measured. The conductivity sensors 68 may include plates, wires, or assume other geometries. In addition, the conductivity sensors 68 may be formed of, for example, titanium. However, it may be appreciated that other materials may be used as well.

Figure 6:
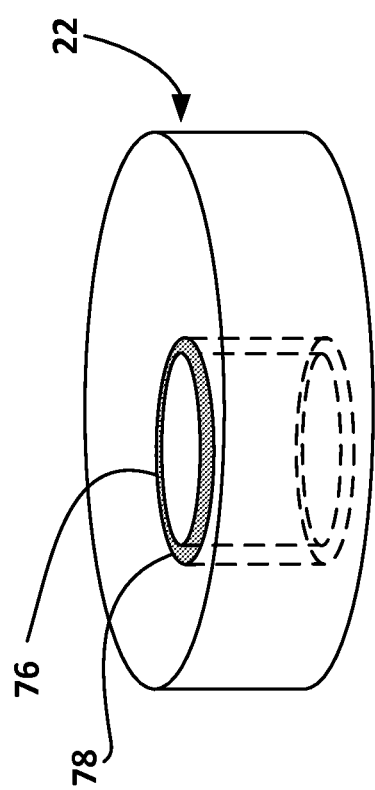
FIG. 6 illustrates an embodiment of a sensor body.

The probes may be at least partially embedded or encapsulated in a sensor body or carrier 22, as illustrated in FIG. 6. The sensor body 22 may be formed from a polymeric material such as acrylic, epoxy, polyethylene, crosslinked polyethylene, ultrahigh molecular weight polyethylene, fluoropolymers such as polytetrafluoroethylene, ethylene tetrafluoroethylene and other materials. The sensor body 22 may be formed around at least a portion of the various sensors or plugs and/or holes may be drilled out of the sensor body 22 to accommodate the probes and thus, the sensor body 22 may have openings 76 defined therein to accommodate the sensors. Furthermore, a sealant, an adhesive or a binder 78 may be used to form a seal between a portion of the individual sensors and the sensor body 22. In some embodiments, the sensor body 22 may be in the range of 10 mm to 75 mm in diameter, including all values and increments therein. In addition, the sensor body 22 may be in the range of 5 mm to 75 mm in thickness, including all values and increments therein. It may be appreciated that some probes may reach outside of the boundaries of the sensor body 22 itself, or, in some embodiments, all the probes may be contained within the bounds of the sensor body 22.

Again, electrical connections 24 for each probe may be provided. Referring again to FIG. 1, the electrical connections may be formed into a ribbon wire, or made through a ribbon wire. As illustrated in one embodiment in FIG. 7, the corrosion sensor 10 may be provided in communication with a data acquisition or recording system 100. Communication between the corrosion sensor 10 and the data acquisition system 100 may be electrical, such as through electrical connections 24. The collection of data by the data acquisition system may be continuous or intermittent. Furthermore, the communication between the corrosion sensor 10 and the data acquisition system 100 may be detachable through the use of various couplings, ports and/or adapters.

In another embodiment illustrated in FIG. 8, the electrical connections 24 from the corrosions sensor 10 may communicate via radio frequency (represented by the dotted line) with a wireless transmitter 102, which may optionally be incorporated into a transceiver. A receiver 104 in communication with a data acquisition system 100 may be provided to receive the corrosion data gathered by the various probes. The wireless transmitter and/or the receiver may be incorporated into transceivers, such that data and/or information may be communicated and/or received from the corrosion sensor 10 and/or the data acquisition system 100.

The data acquisition may include or be limited to, for example, recording media 110, which may include non-volatile storage such as flash memory, EPROM, etc, see FIG. 8. In other embodiments the data acquisition system 100 may also include a processor 112 and/or a variety of inputs and/or outputs 114, which may include control devices such as keyboards or mouse, other recording media, other sensors, etc. In other embodiments, the data acquisition system may also include a galvanostat, a galvanometer, a potentiometer, or a potentiostat.

Examples

The examples herein are for purposes of illustration and are not meant to limit the scope of the description herein or claims appended here to.

Chloride Probe

A chloride probe was manufactured using the thermal melt method, in which a layer of AgCl was deposited onto a commercially pure (at least 99.0%) Ag rod by hot-dipping in molten AgCl bath at a temperature of 455° C. The dipping process was conducted four times to obtain a relatively more compact and smooth AgCl coating. The electrode was then rinsed with acetone and dried. An electrical connection was made to the electrode via a copper wire, which was later covered in an epoxy resin. The nominal exposed area of the electrode was 1 cm². The treated electrode was encapsulated in a polyethylene cell filled with saturated $KNO_3$. Porous zirconium powder (−20+60 mesh) was used to form a porous junction in the cell. The porous zirconium may aid in protecting the Ag/AgCl electrode and minimize the penetration of $OH^-$ ions into the cell from the surrounding environment.

Three chloride probes were immersed in a number of simulated concrete pore solutions. Table 1 describes the nominal chemical composition and pH. It is noted that SPS2 was used for pH probe calibration only. The test cell was normally sealed to minimize solution carbonation, except when chlorides were added to the solution. A saturated calomel electrode (SCE), used as a reference was also immersed in the solutions. The chloride sensing probes and the SCE were connected to a multi-channel potentiostat to record the open circuit potential versus time. The open circuit potential measurements herein were calibrated to the SCE scale, unless otherwise noted. The chloride concentration was increased stepwise at selected time intervals and later decreased to monitor electrode sensitivity.

TABLE 1

Nominal chemical composition and pH of simulated concrete pore solutions.

| Solution | Nominal pH | NaOH g/L | KOH g/L | Ca(OH)$_2$ g/L | Na$_2$CO$_3$ g/L | NaHCO3 g/L |
|---|---|---|---|---|---|---|
| CPS | 9.7 | — | — | — | 4.21 | 2.66 |
| SPS 1 | 13.3 | 3.7 | 10.5 | 2.0 | — | — |
| SPS 2 | 13.6 | 8.33 | 23.3 | 2.0 | — | — |
| SCS | 12.6 | — | — | 2.0 | — | — |
| SPS 4 | 11.6 | 0.0833 | 0.233 | — | — | — |

Figure 9B:
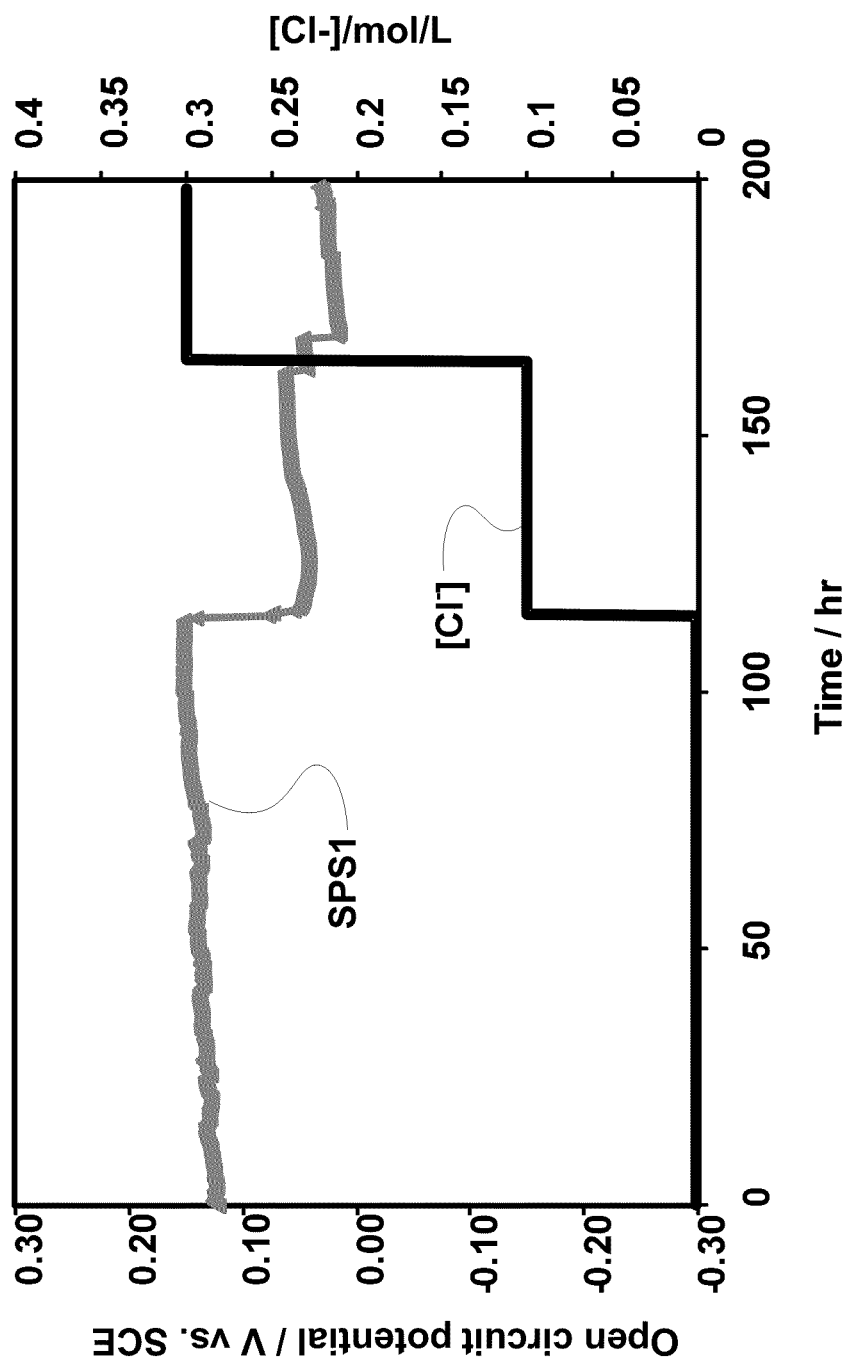
FIG. 9b illustrates the open current potential versus voltage over a period of approximately 500 hours, wherein chloride ions are introduced over the time period for simulated concrete pour solution SPS1.

The open circuit potential was recorded for 21 days for each probe at 23+/−2° C. FIGS. 9a and 9b illustrate the average open circuit potentials computed from measurements of the three independent chloride probes. For the first 100 hours of exposure and for chloride concentrations of less than 0.01 mol/L, the open circuit potentials for all solutions were relatively unstable. For chloride concentrations of 0.01 mol/L to 1.0 mol/L, the chloride probes exhibited relatively goods sensitivity and relatively fast stabilization for both increases and decreases in chloride concentration.

Figure 10A:
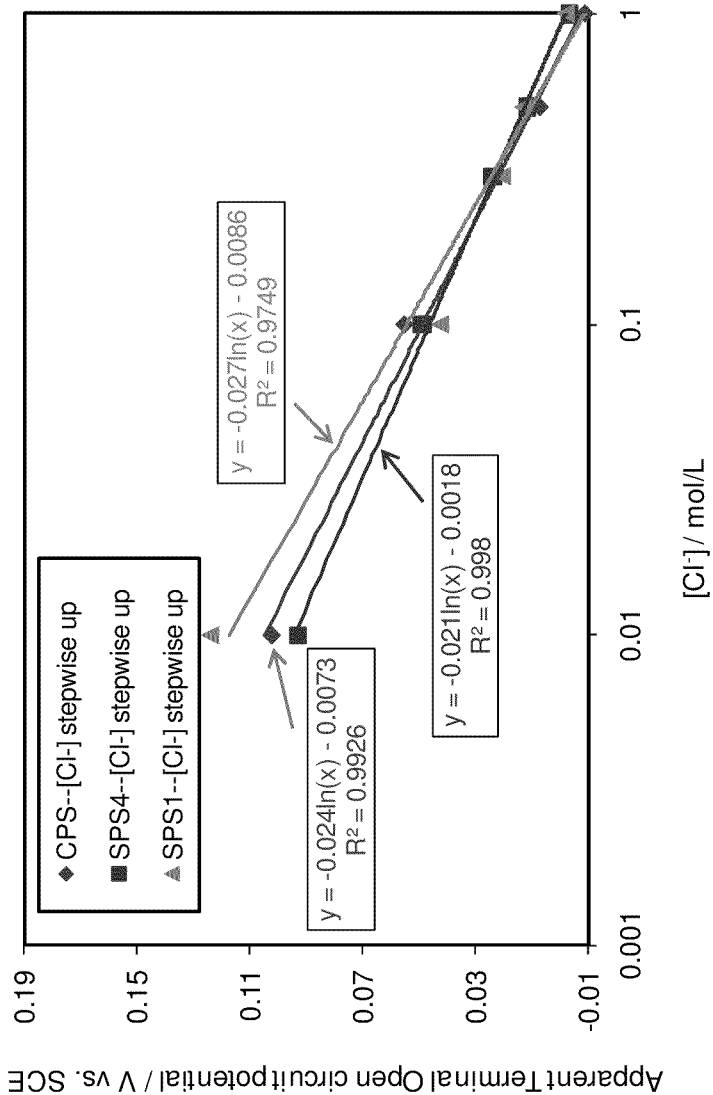
FIG. 10a illustrates the change in apparent terminal open circuit potential versus voltage for stepwise up additions of chloride ions.
Figure 10B:
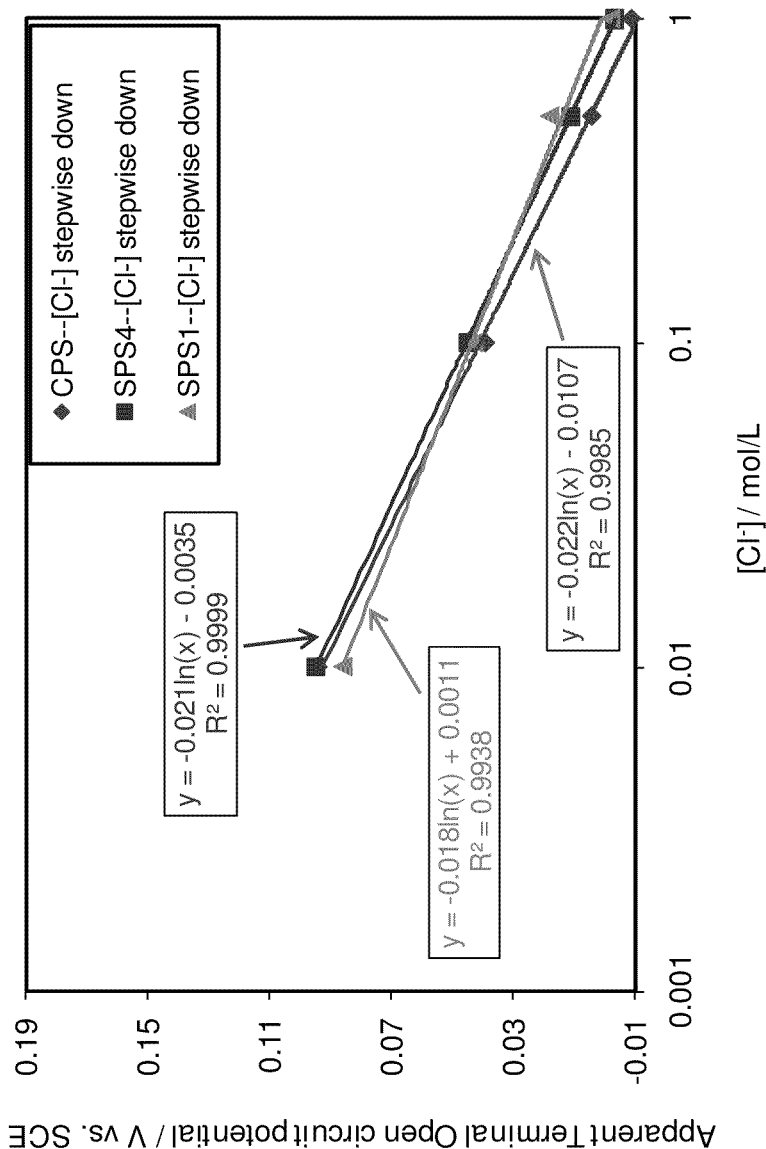
FIG. 10b illustrates the change in apparent terminal open circuit potential versus voltage for stepwise down changes of chloride ions.

The apparent terminal open circuit potentials as a function of the logarithm (base 10) of chloride concentration for each solution was tested. The results show linear trends in all cases with correlation coefficients close to unity over the 0.01 mol/L to 1.0 mol/L chloride concentration range for both the stepwise increase FIG. 10a and stepwise decrease FIG. 10b of chloride concentration. The testing also illustrated that the chloride probe is pH independent for the pH range examined.

Figure 11:
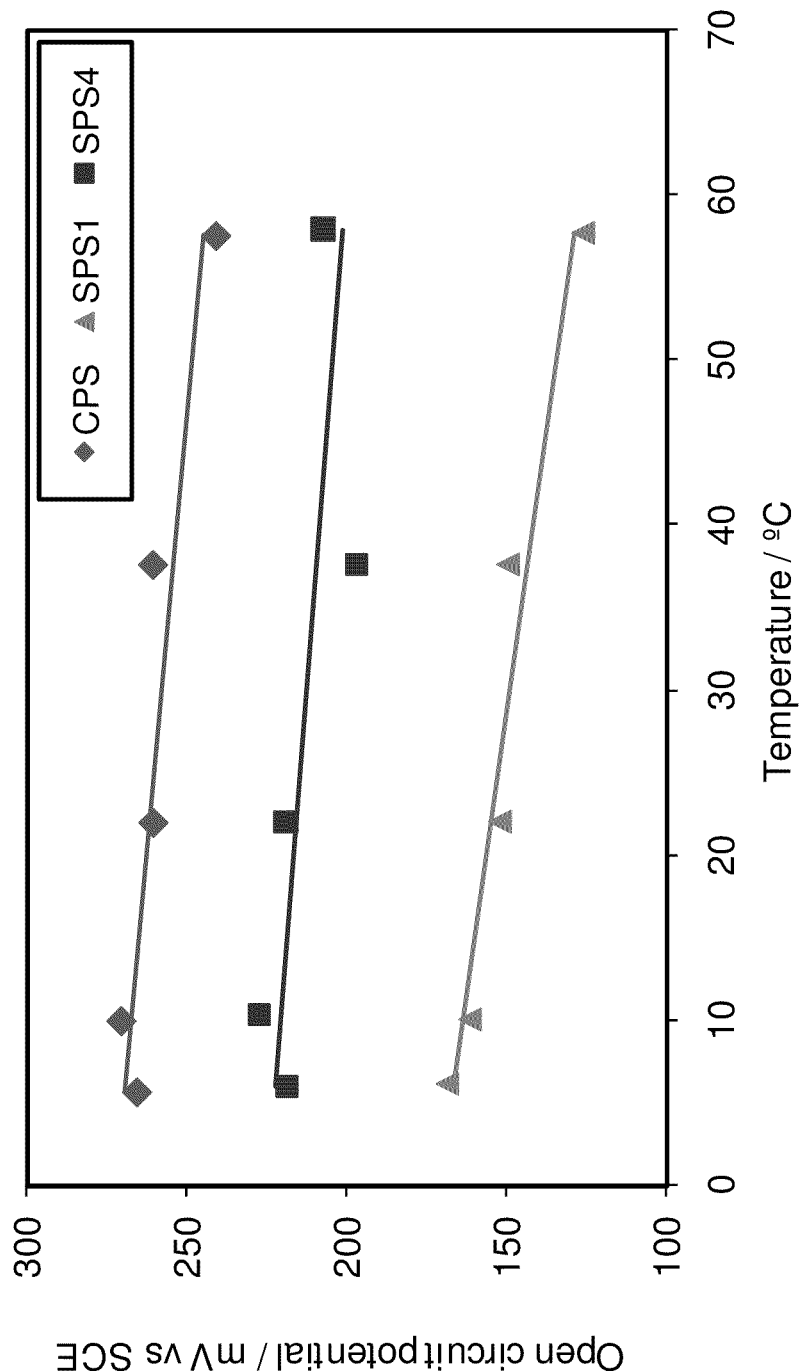
FIG. 11 illustrates the change in open circuit potential versus temperature.

Temperature dependence of the chloride probes were examined. As can be seen in FIG. 11, as the temperature increases, the open circuit potentials in all solutions decrease, relatively consistent with Nerstian behavior. The potential shifts are less than 40 mV for a temperature range of 5° C. to 60° C. in all simulated concrete solutions tested, i.e., CPS, SPS1 and SPS4.

pH Probe

A flat 0.5 inch by 0.25 inch specimen of $Ir_2O_3/Ta_2O_5$ was provided as the pH probe. Four probes were individually immersed in solution a sealed glass cell maintained at 10° C., 25° C., 40° C. and 60° C. A SCE was used as a reference in each solution. The pH sensing probes and the SCE electrode were connected to a multi-channel potentiostat to record the open circuit potential versus time. The actual pH values of the simulated concrete pour solutions were experimentally measured using a Fisher Scientific ACCUMET pH/conductivity meter.

Figure 12:
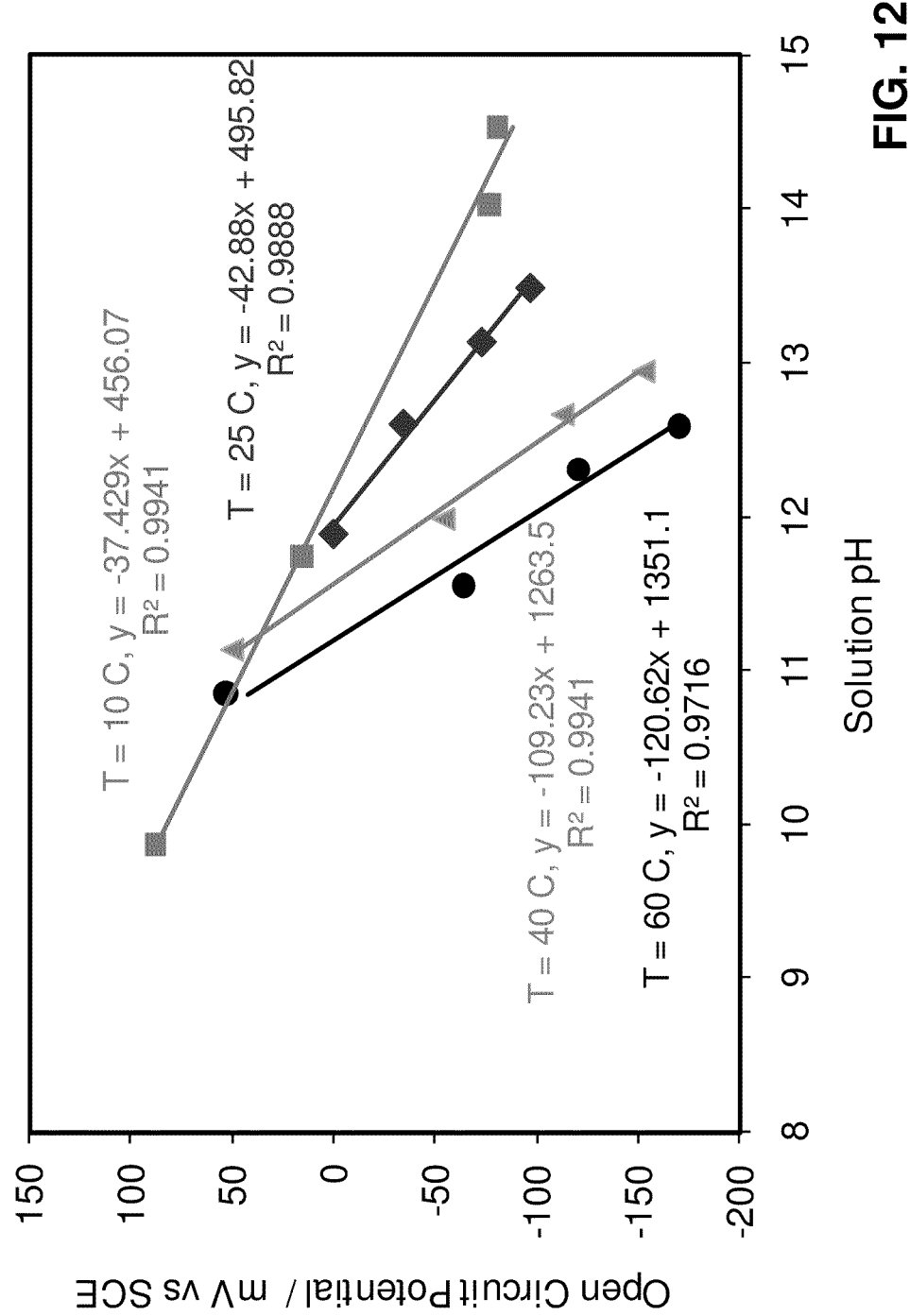
FIG. 12 illustrates the change in open circuit potential versus pH at 10° C., 25° C., 40° C. and 60° C.

FIG. 12 shows the correlation between the open circuit potential and the pH of the simulated concrete pour solutions at 10, 25, 40 and 60° C. As can be seen in the figure, the trends appeared to be relatively linear with correlation coefficients of greater than 0.97. As the temperature increases, the pH in the tested solutions decreases, relatively consistent with Nerstian behavior.

Corrosion Rate Probe

The corrosion rate probe is a multi-electrode array sensor probe fabricated of 16 sensing elements made of 0.1 cm diameter 1018 carbon steel wires separated 0.2 cm measured from center to center of each electrode. The wires were embedded in an epoxy matrix, product number: 2300 from Aremco Products, Inc. The epoxy matrix was formed into a 1 cm diameter and 0.5 cm thick puck. The epoxy material exhibits a temperature resistance of −55° C. to 175° C. The external wiring that connected the sensor to the wireless unit was made of SMB cable plugs RG 196 A/U to minimize potential electromagnetic artifacts. Prior to each test, the sensing surface of the sensors were polished using an aqueous solution and 600-grit paper and cleaned with ethanol.

The multi-array sensor probe was initially placed in contact with laboratory air for 2 hours to determine the baseline conditions of the probe. The sensor was then immersed in the SPS1 solution maintained at 23° C. for up to 100 hours. Reagent grade NaCl powder was added periodically to the solution and the corrosion current density was periodically recorded using a multi-array sensor acquisition unit provided by Aginova, Inc. For comparison, two 5 inch long #5 carbon steel bars were immersed in the same cell. Linear polarization resistant (LPR) technique was used to measure the corrosion rates of the bars after each chloride addition.

Figure 13:
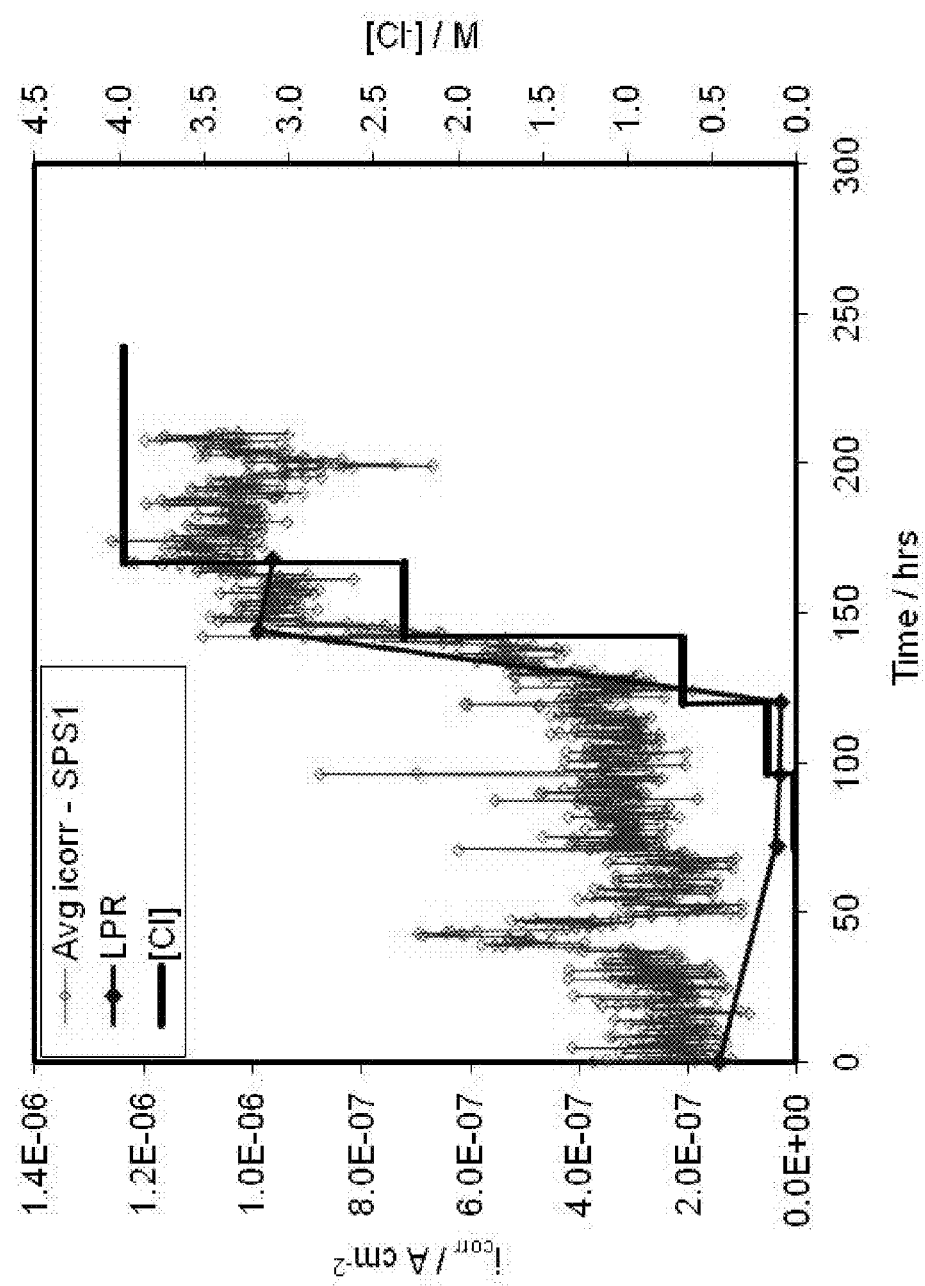
FIG. 13 illustrates measured corrosion current density as a function of time and chloride ions concentration in simulated concrete pour solution SPS1 as measured by an embodiment of a multiple array sensor probe and LPR.

FIG. 13 shows the evolution of corrosion current density obtained by the multiple-array sensor probe and the LPR technique (using the average value for two bars) as a function of time. It would appear from the figure that when the chloride concentrations are less than 0.2 mol/L, the corrosion current density obtained by the multiple array sensor probe and the LPR technique were comparable (i.e., $1\times10^{-7}$ to $4\times10^{-7}$ A/cm$^2$). At chloride concentrations of greater than about 2.5 mol/L, the corrosion current density obtained by both multiple array sensor probe and LPR technique increased to $1\times10^{-6}$ to $1.2\times10^{-6}$ A/cm$^2$ and remained nearly constant, even after the subsequent chloride additions.

Sensor Body

Figure 14:
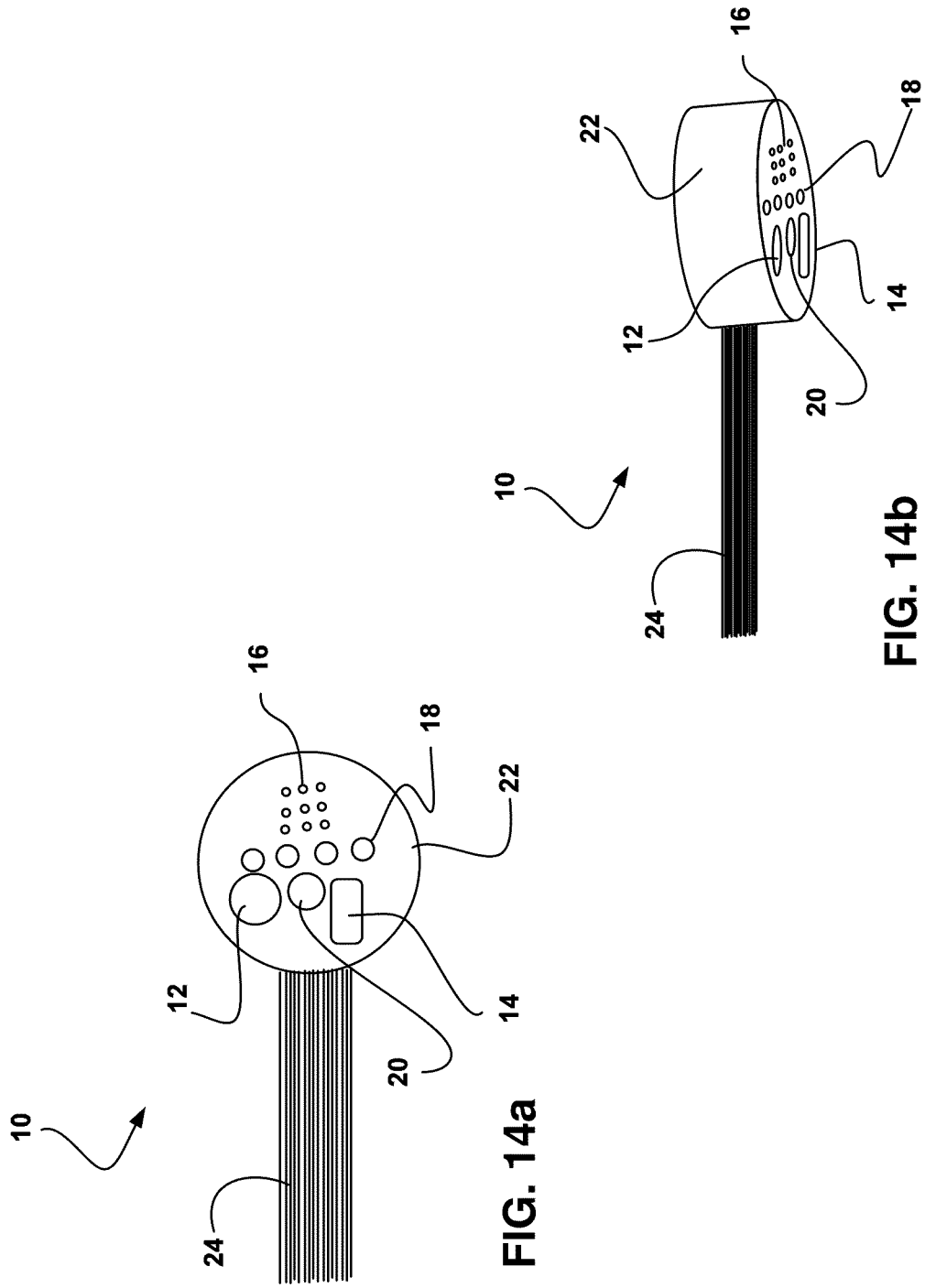
FIGS. 14a and 14b illustrate top and side perspective views, respectively, of an embodiment of a corrosion sensor.

A prototype sensor, illustrated in FIGS. 14a and 14b was designed to simultaneously measure corrosion rate, chloride concentration, pH and resistivity in concrete pore solutions. The sensor body 22 was formed into an acrylic plug. Inserted into the sensor body is a 0.5 inch diameter chloride sensing probe 12, a 0.25 inch diameter circular graphite bar 20 used as a common reference electrode for both pH and chloride measurements, a 0.5 inch by 0.25 inch pH probe 14 and a 1 inch diameter multiple array sensor probe 16. The multiple array sensor probe included 9 sensing electrodes of 0.1 cm in diameter made of 1018 carbon steel with 2.0 mm separated from center to center of each electrode. The multiple array sensing elements 56 were coated in an epoxy and individually inserted into matching holes drilled in the acrylic. The sensor body 22 itself was 1.5 inches in diameter by 0.75 inches in thickness. A ribbon cable was used for sensor electrical connections.

Cement paste cylinders were then prepared according to ASTM C31/C31M-03a standard procedures. The selected mix design was 0.6215 Kg of Type I Portland cement, 2.0 kg of water and 98.9 g of NaCl. The chloride ions were added as part of the mixing water. Two 5 inch long #5 bars were cast in the cylinder for LPR measurements. The exposure area of each #5 bar was 31.7 cm$^2$.

Figure 15:
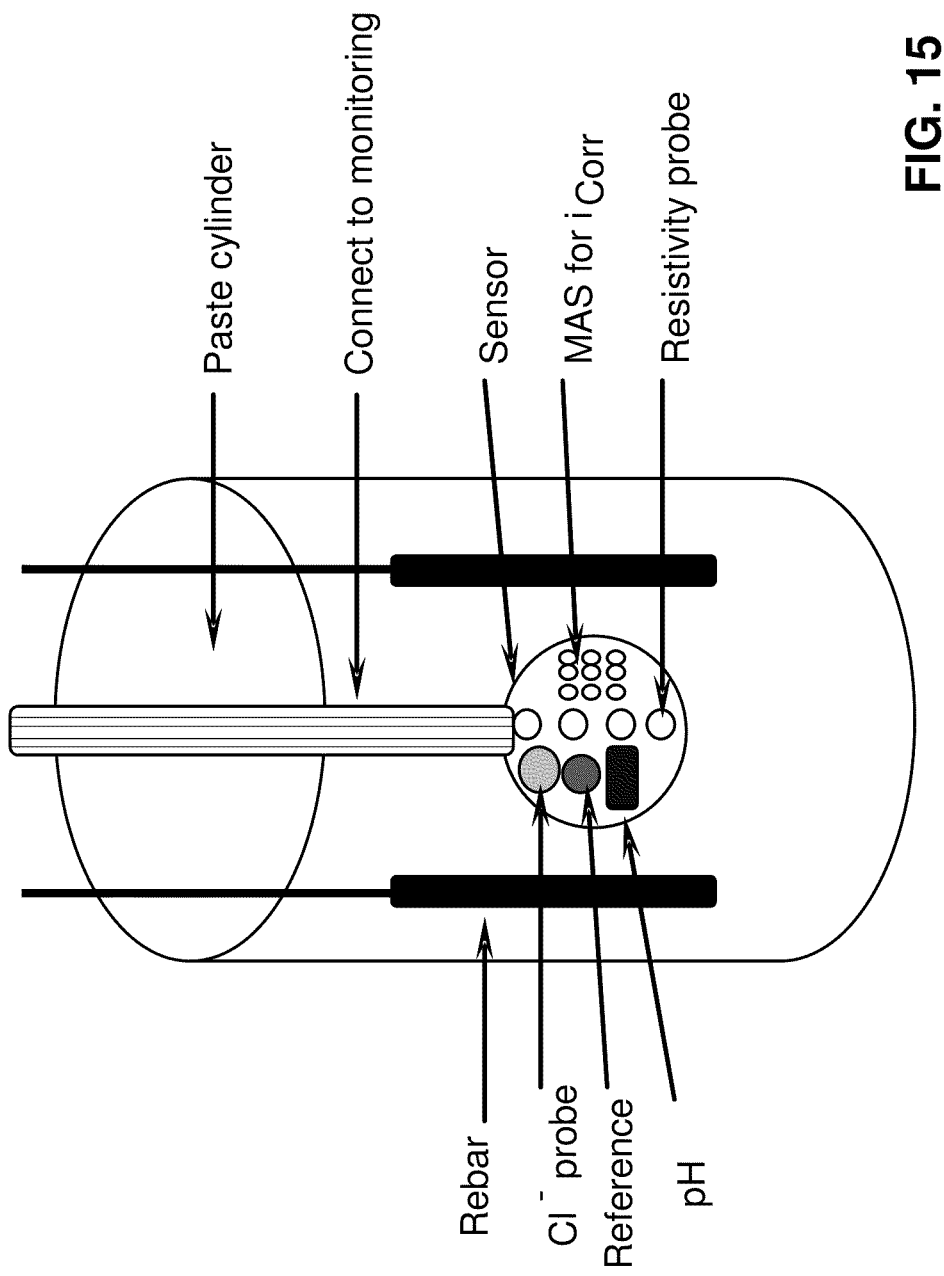
FIG. 15 illustrates a schematic of a cement paste cylinder with an embedded sensor package.

A schematic of the cement paste cylinder with the sensor package is illustrated in FIG. 15. After casting, the cylinders were cured in a plastic mold for 24 hours. Subsequently, the cylinders were removed and partially immersed in a container filled with tap water, maintained at room temperature. Open circuit potential measurements obtained by the chloride and pH probes were measured with respect to the graphite electrode and converted to the SCE scale. An SCE electrode was placed on top of a wet sponge at the cylinder surface for potential conversion. The readings were recorded using a FLUKE 179 multimeter. Concurrently, corrosion rates were measured with the multiple array sensor probe and collected every 15 minutes.

Figure 16A:
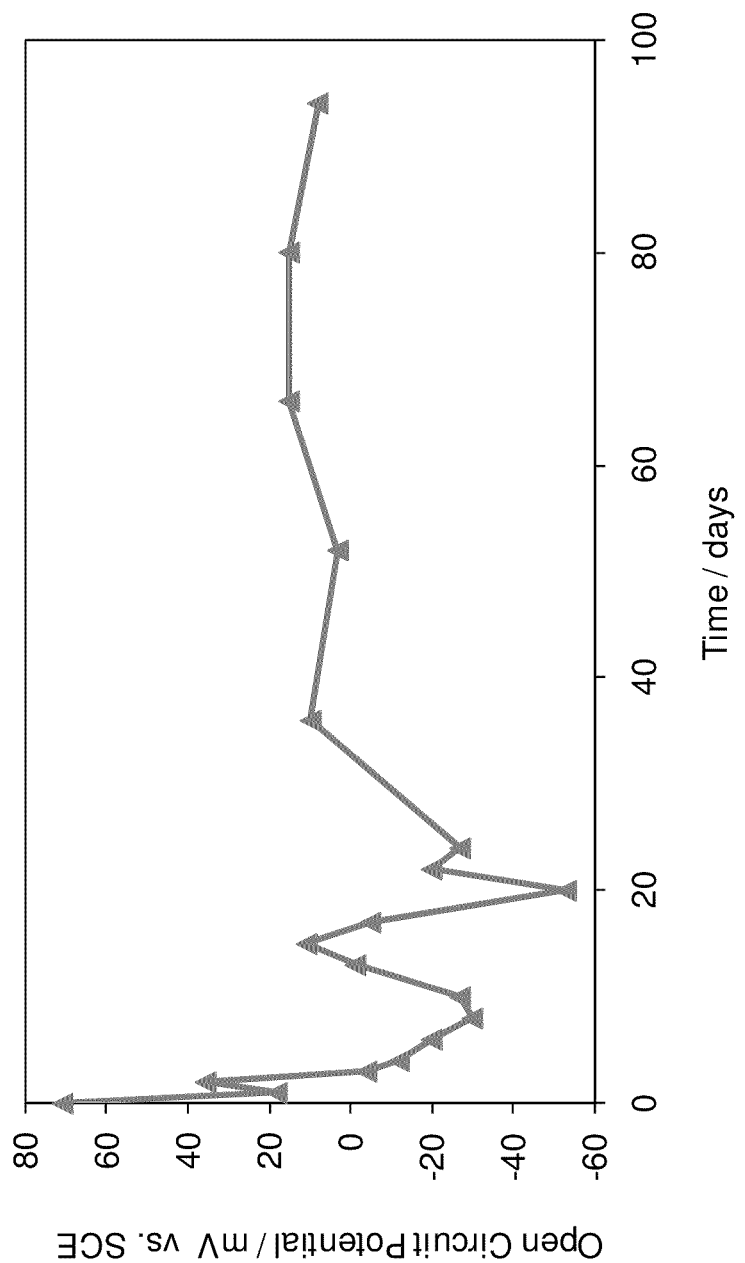
FIG. 16a illustrates the open circuit potential over time of a chloride probe in an embodiment of a corrosion sensor.
Figure 16B:
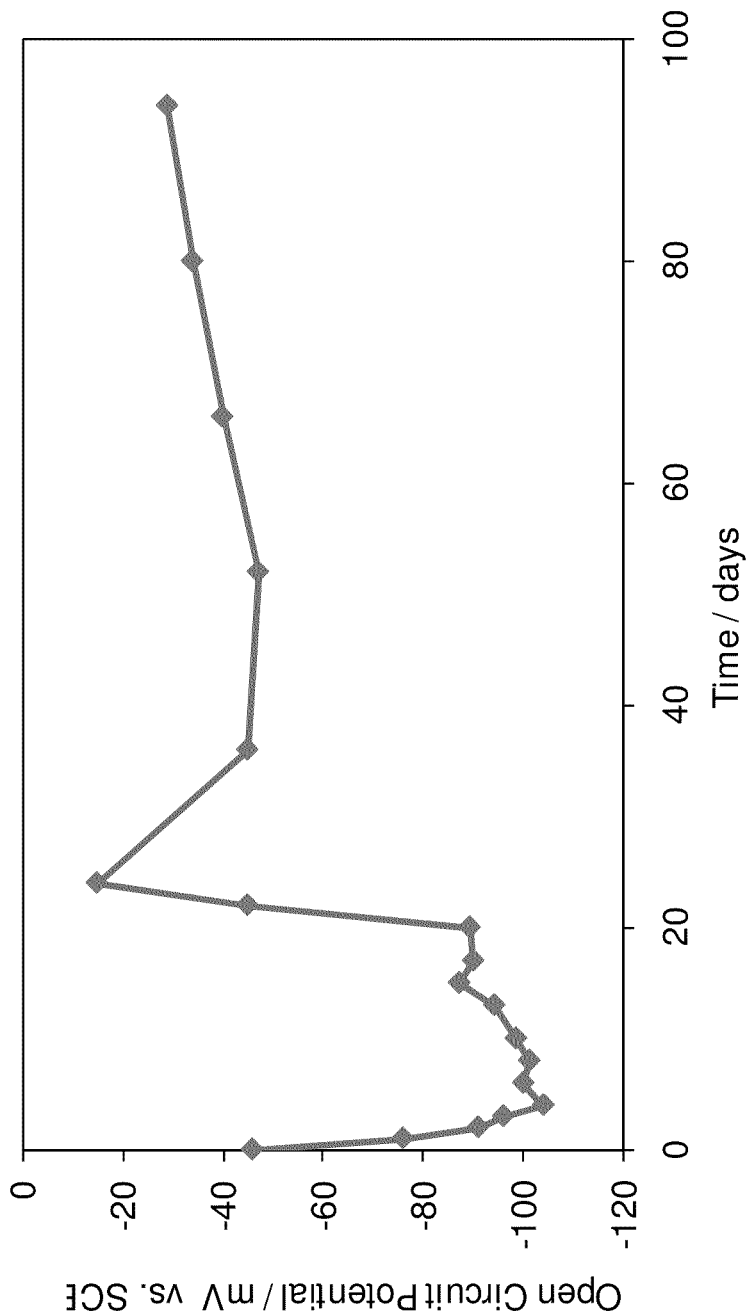
FIG. 16b illustrates the open circuit potential over time of a pH probe in an embodiment of a corrosion sensor.

After approximately 90 days of exposure, the pH and chloride probes attained nearly terminal open circuit potentials of 10 mV vs. SCE for the chloride probe, as illustrated in FIG. 16a and approximately −30 mV vs. SCE for the pH probe, as illustrated in FIG. 16b. The graphite bars placed in the sensor body as a reference electrode exhibited a relatively constant potential of approximately −120 mV vs. SCE after 25 days of exposure. Accordingly to the pH calibration curves in FIG. 12, the pH of the cement paste cylinder at the sensor package location was 12.3, which appeared to be consistent with pH values recorded in concrete contaminated with significant amount of chlorides. In addition, with reference to FIG. 6, the free chloride concentration in the cement past pore water recorded by the sensor was approximately 0.45 mol/L. The expected free chloride concentration in the cement past pore solution would range from 0.1 mol/L to 0.5 mol/L, which is in agreement with the chloride value obtained by the sensor.

Figure 17:
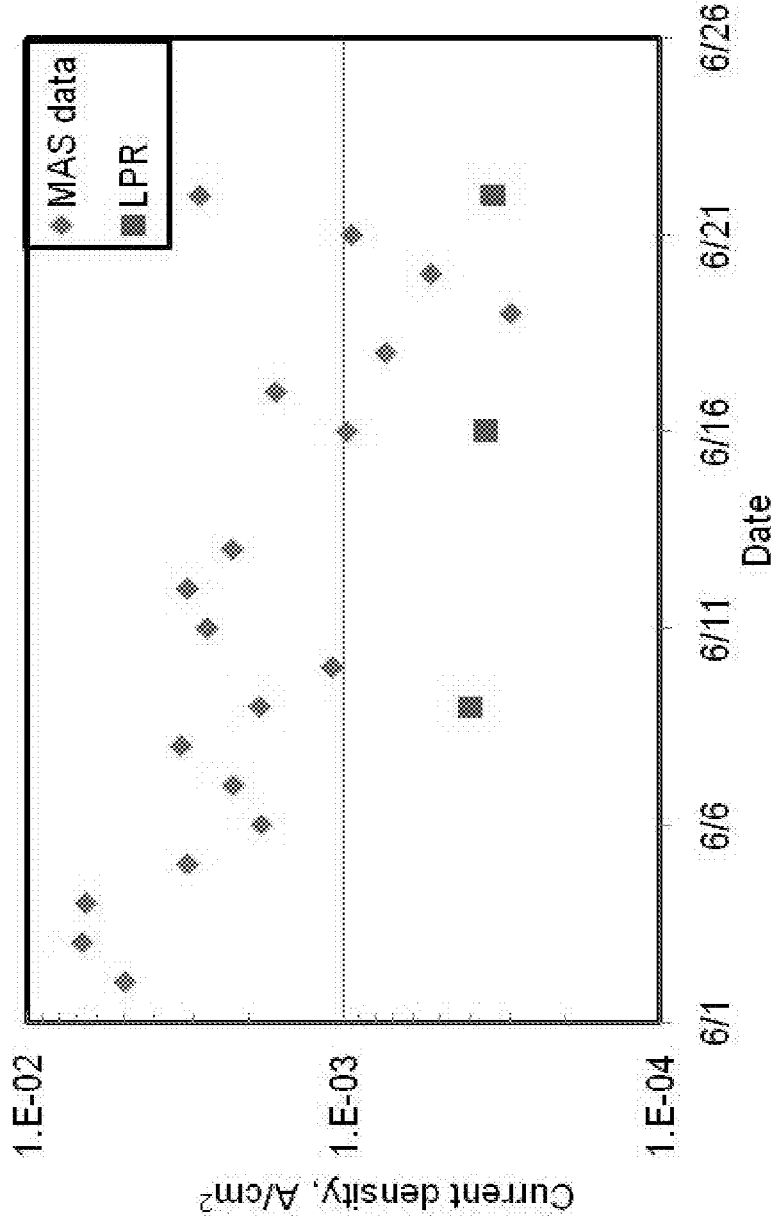
FIG. 17 illustrates corrosion current density obtained by the multiple array sensor in an embodiment of a corrosion sensor and as obtained by LPR.

FIG. 17 illustrates a comparison of the corrosion current densities (or rate) obtained by the multiple array sensor probe and those attained by the LPR technique conducted on the bars embedded in the cement paste cylinders. The figure indicates that during the first three weeks the corrosion rate measured by the multiple array sensor probe was about one order of magnitude greater than that recorded by LPR. As time progressed, the corrosion rates measured by both the multiple array sensor probe and the LPR were relatively comparable.

Also provided herein is a method of measuring corrosion in a reinforced concrete structure. The method may include inserting a corrosion sensor into a reinforced concrete structure. One or more corrosion sensors, as described above may be positioned within the reinforced concrete structure before or while the concrete is poured around the reinforcing structure. As may be appreciated the sensor may be positioned at multiple depths relative to the exterior surface of the reinforced concrete structure as well as at various distances relative to the reinforcement structure itself. In addition, sensors may be provided in locations that may be more prone to corrosion, such as in locations underwater, or exposed to drainage run off, etc.

Various aspects of corrosion may be monitored. For example, in one embodiment chloride ions may be measured with a chloride probe, pH may be measured with a pH probe, resistivity may be measured with a resistivity probe and corrosion density may be measured with a multiple array sensor. Monitoring may be performed on a continuous or periodic basis. In periodic monitoring, monitoring may be performed at regular intervals or sporadically, depending on, for example, the requirements of the structure. In some embodiments, monitoring may be periodic until at least one critical point is reached with regard to at least one aspect of corrosion and then either the monitoring interval may be increased or monitoring may become continuous. A critical point may be understood as a point that indicates that the passive layer on the reinforced structure has been or is close to being permeated, breached or eliminated leading to further corrosion of the reinforced structure.

As may be appreciated the corrosion sensor may be provided in combination with a data acquisition system for obtaining and/or analyzing the data from the corrosion sensor. Accordingly, a system may be provided for monitoring corrosion in a reinforced concrete structure, which may include at least one corrosion sensor, including a sensor body, a chloride probe, a pH probe held in said sensor body, a reference electrode for said chloride probe, a multiple array sensor, and a resistivity probe all held in the sensor body. In addition, the system may include a data acquisition system in communication with said at least one corrosion sensor.

The foregoing description of several methods and embodiments has been presented for purposes of illustration. It is not intended to be exhaustive or to limit the claims to the precise steps and/or forms disclosed, and obviously many modifications and variations are possible in light of the above teaching. It is intended that the scope of the invention be defined by the claims appended hereto.

What is claimed is:

1. A corrosion sensor, comprising:
  a sensor body comprising a polymeric material including a plurality of openings therein;
  a chloride probe partially embedded within one of said openings in said sensor body;
  a pH probe partially embedded within one of said openings in said sensor body;
  a reference electrode for said chloride probe and said pH probe partially embedded within one of said openings in said sensor body;

a multiple array corrosion rate sensor partially embedded within one of said openings in said sensor body, wherein said multiple array sensor includes two or more sensing elements having a diameter in the range of 0.01 cm to 1.0 cm and a length in the range of 0.01 cm to 10 cm, wherein said sensing elements are exposed at a tip of each sensing element as well as along a portion of a shaft of each sensing element;

a resistivity probe partially embedded within one of said openings in said sensor body; and a sealant in each of said openings formed between a portion of each of said probes, electrode, and array sensor and said sensor body, and spanning and surrounding the portions of each of said probes, electrode, and array sensor.

2. The sensor of claim 1, wherein said chloride probe comprises a Ag/AgCl electrode.

3. The sensor of claim 1, wherein said chloride probe includes a cell and within said cell is saturated $KNO_3$ gel.

4. The sensor of claim 1, wherein said chloride probe includes a cell, a cell wall defining said cell and a porous junction provided in said cell wall.

5. The sensor of claim 4, wherein said porous junction comprises porous zirconium powder.

6. The sensor of claim 1, wherein said pH probe comprises a $Ir_2O_3/Ta_2O_5$ pH sensing body.

7. The sensor of claim 1, wherein said reference electrode is graphite.

8. The sensor of claim 1, wherein said reference electrode is common to said chloride probe and said pH probe.

9. The sensor of claim 1, wherein said resistivity probe comprises two or more conductivity sensors.

10. The sensor of claim 1, wherein said resistivity probe comprises four conductivity sensors.

11. The sensor of claim 1, wherein said sensing elements include 1018 carbon steel.

12. The sensor of claim 1, wherein said sensor further comprises electrical ports electronically connected to each of said probes, electrodes and array sensor capable of establishing electrical communication with a data acquisition system.

13. The sensor of claim 1, wherein said sensor further comprises a wireless component electronically connected to each of said probes, electrodes and array sensor capable of establishing wireless communication with a data acquisition system.

14. A method of measuring corrosion in a reinforced concrete structure, comprising:

inserting a corrosion sensor into a reinforced concrete structure embedded at a distance from a reinforcing structure of said reinforced concrete structure, wherein said corrosion sensor comprises a sensor body comprising polymeric material including a plurality of openings therein, a chloride probe partially embedded within one of said openings in said sensor body, a pH probe partially embedded within one of said openings in said sensor body, a reference electrode for said chloride probe and said pH probe partially embedded within one of said openings in said sensor body, a multiple array corrosion rate sensor partially embedded within one of said openings in said sensor body, wherein said multiple array sensor includes two or more sensing elements having a diameter in the range of 0.01 cm to 1.0 cm and a length in the range of 0.01 cm to 10 cm, wherein said sensing elements are exposed at a tip of each sensing element as well as along a portion of a shaft of each sensing element, a resistivity probe partially embedded within one of said openings in said sensor body, and a sealant in each of said openings formed between a portion of each of said probes, electrode, and array sensor and said sensor body, and spanning and surrounding the portions of each of said probe, electrode, and sensor; and monitoring chloride ions with said chloride probe, pH with said pH probe, resistivity with said resistivity probe and corrosion density with said multiple array corrosion rate sensor.

15. The method of claim 14, wherein said monitoring is continuous.

16. The method of claim 14, wherein said monitoring is periodic.

17. The method of claim 14, wherein said corrosion sensor is in communication with a data acquisition system.

18. A system for monitoring corrosion in a reinforced concrete structure, comprising:

at least one corrosion sensor embedded in a reinforced concrete structure at a distance from a reinforcing structure of said reinforced concrete structure, including a sensor body comprising a polymeric material including a plurality of openings therein, a chloride probe partially embedded within one of said openings in said sensor body, a pH probe partially embedded within one of said openings in said sensor body, a reference electrode for said chloride probe and said pH probe partially embedded within one of said openings in said sensor body, a multiple array corrosion rate sensor partially embedded within one of said openings in said sensor body, wherein said multiple array sensor includes two or more sensing elements having a diameter in the range of 0.01 cm to 1.0 cm and a length in the range of 0.01 cm to 10 cm, wherein said sensing elements are exposed at a tip of each sensing element as well as along a portion of a shaft of each sensing element, a localized concrete resistivity probe partially embedded within one of said openings in said sensor body, and a sealant in each of said openings formed between a portion of each of said probes, electrode, and sensor and said sensor body, and spanning and surrounding the portions of each of said probe, electrode, and sensor; and a data acquisition system in communication with said at least one corrosion sensor.

* * * * *